United States Patent [19]

Kaster

[11] 4,368,736

[45] Jan. 18, 1983

[54] ANASTOMOTIC FITTING

[76] Inventor: Robert L. Kaster, 2730 Vagabond La., Plymouth, Minn. 55447

[21] Appl. No.: 207,677

[22] Filed: Nov. 17, 1980

[51] Int. Cl.$^3$ ............................................. A61B 17/11
[52] U.S. Cl. ............................................... 128/334 C
[58] Field of Search ............... 128/334 C, 334 R, 283; 3/1.4

[56] References Cited

U.S. PATENT DOCUMENTS

| | | | |
|---|---|---|---|
| 2,453,056 | 11/1948 | Zack | 128/334 C |
| 3,435,823 | 4/1969 | Edwards | 128/334 C |
| 3,456,965 | 7/1969 | Gajewski et al. | 128/334 C X |
| 3,540,451 | 11/1970 | Zeman | 128/334 R |
| 3,908,662 | 9/1975 | Razgucov et al. | 128/334 C X |

*Primary Examiner*—Michael H. Thaler
*Attorney, Agent, or Firm*—Hugh D. Jaeger

[57] ABSTRACT

Anastomotic fitting for coronary artery bypass graft surgery having an assembly of components including a flanged tube having a longitudinal hole running therethrough and projections extending outwardly therefrom, an aortic wall attachment ring having a plurality of dual-tined anchors positioned about spacers on a closed ring, a graft fixation collaring having two component parts and having recessed circumferential grooves for accepting springs, ligatures, or split-ring clamps. At surgical implantation, all components of the anastomotic fitting engage together forming an integral anastomotic fitting where the flange of the flanged tube engages against an inside wall of an aorta, the tines engage the aortic wall from the outside wall of the aorta, and a saphenous vein or vascular graft engages between the tube and the graft fixation collar.

16 Claims, 10 Drawing Figures

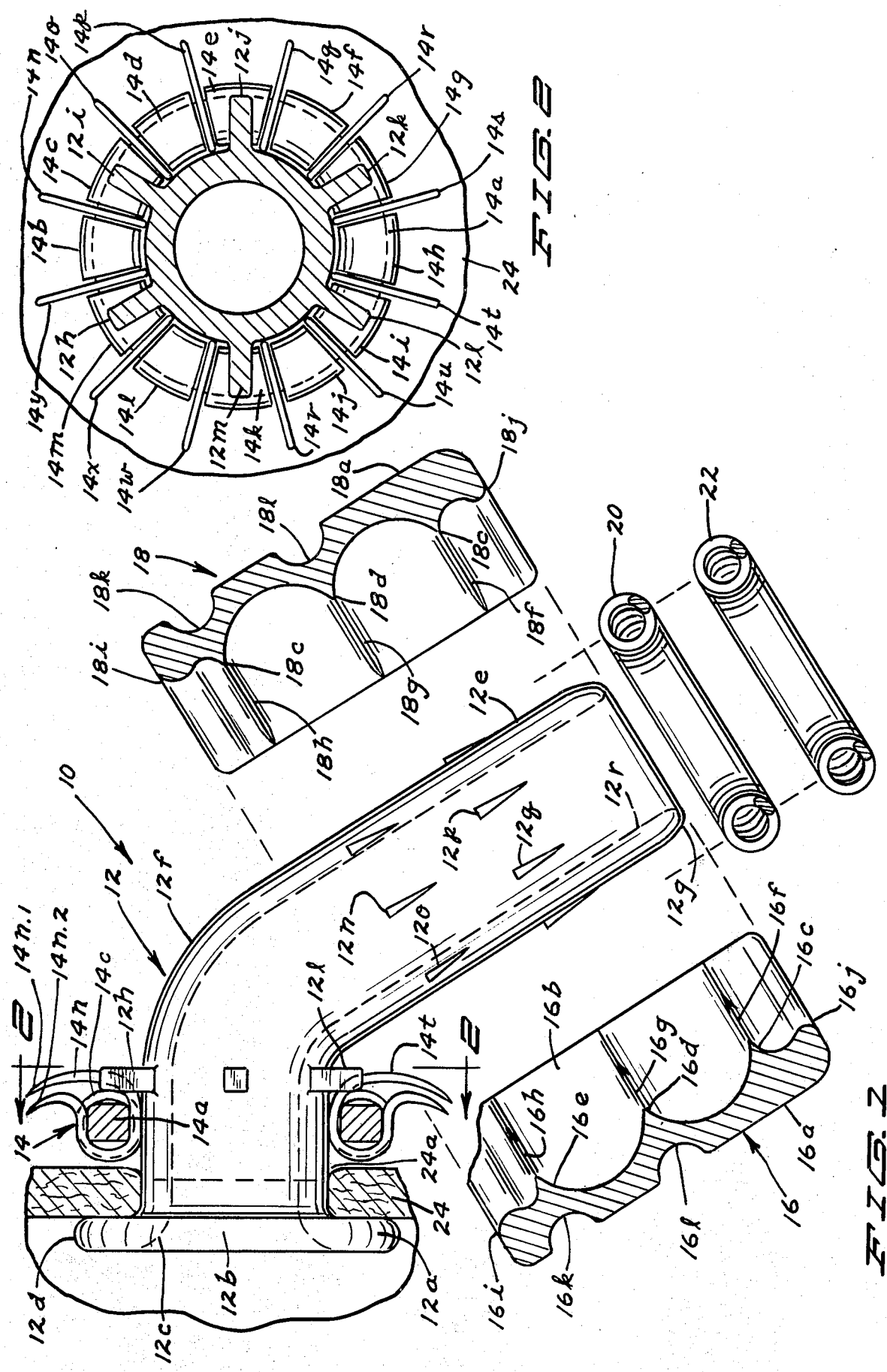

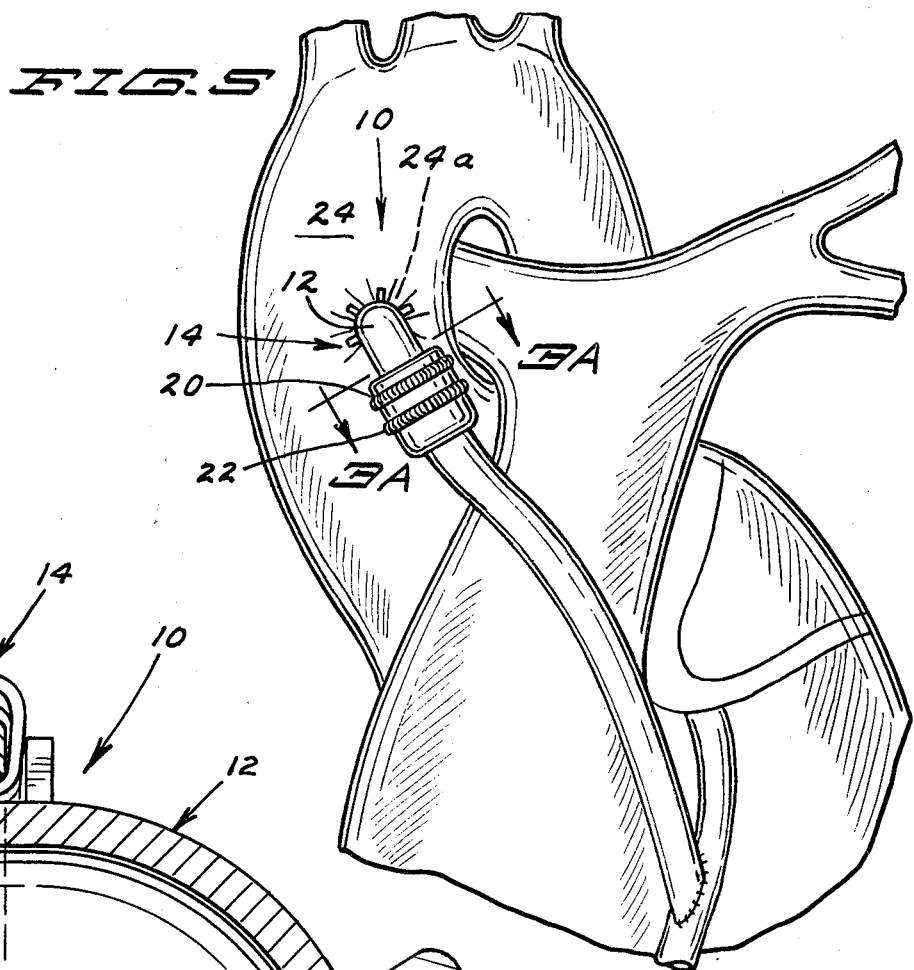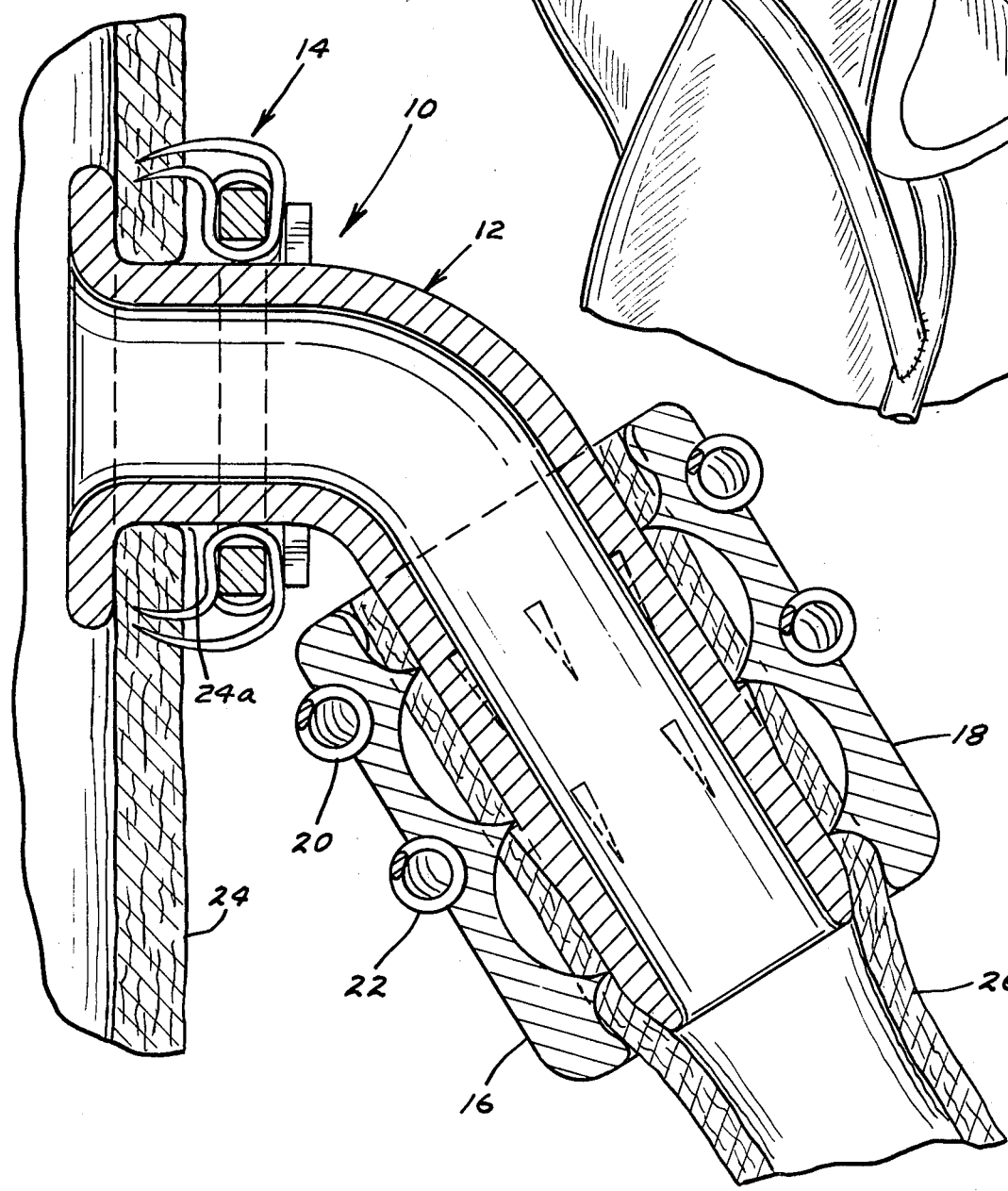

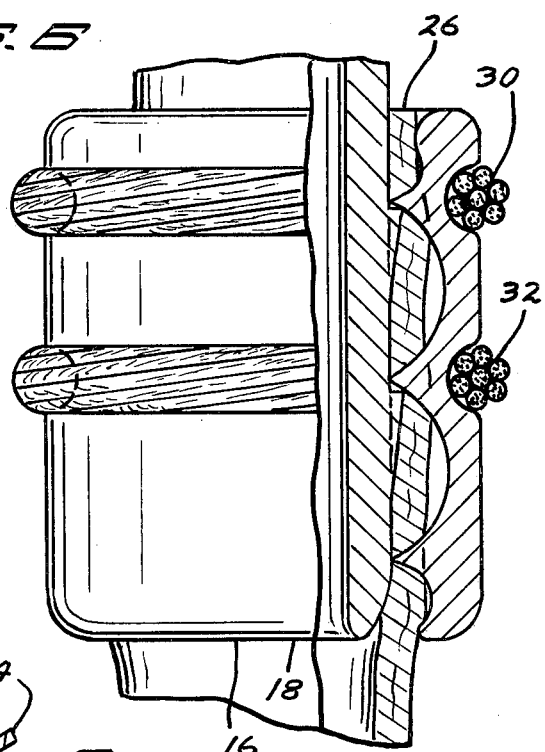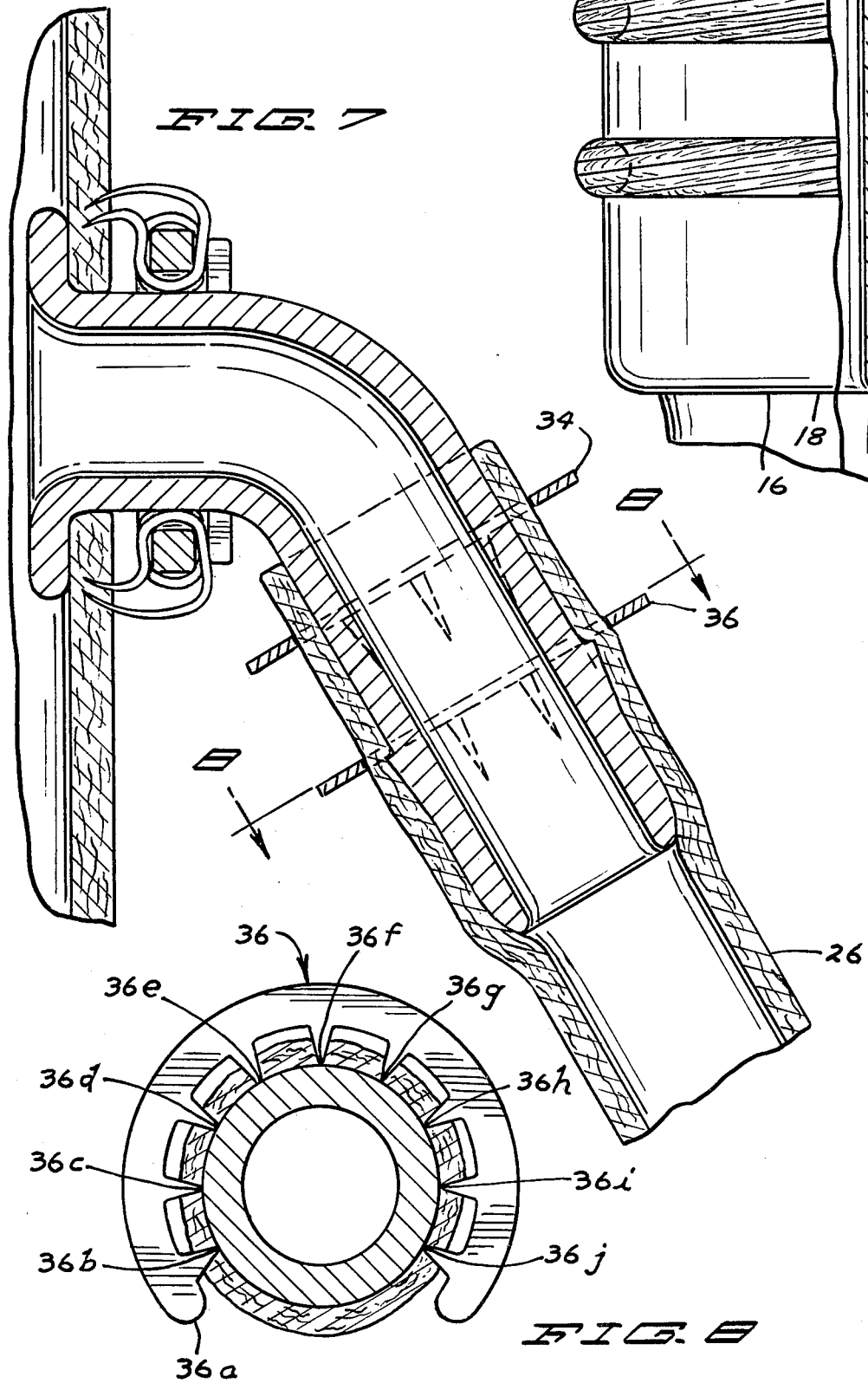

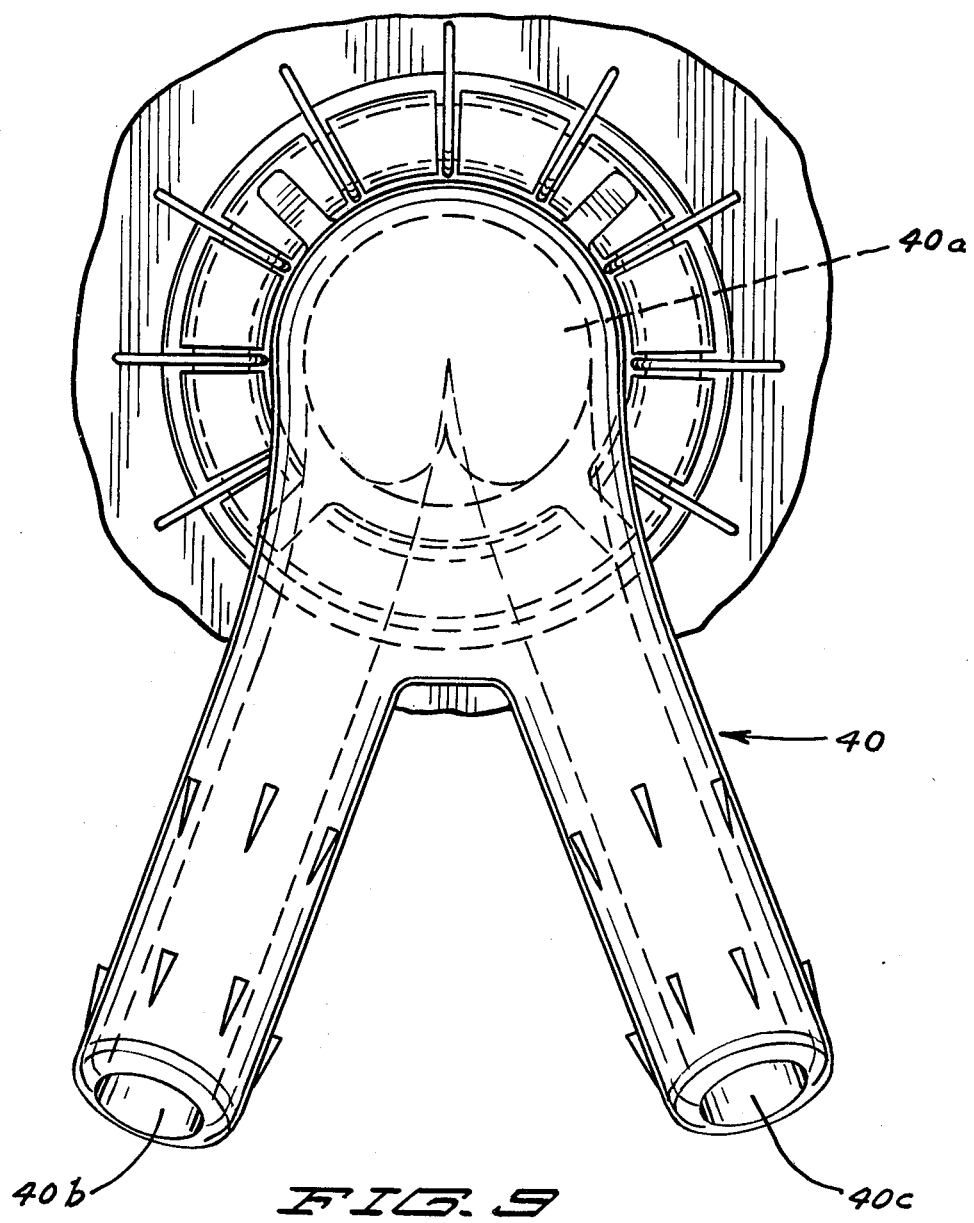

ANASTOMOTIC FITTING

BACKGROUND OF THE INVENTION

1. Field of the Invention

The present invention pertains to a surgical prosthesis, and, more particularly, pertains to an anastomotic fitting for connecting a vascular graft to the ascending aorta.

2. Description of the Prior Art

Diseases affecting the cardiovascular system are either congenital or acquired. An acquired cardiovascular disease can result from living habits, infections or injuries during embryonic life, or at any time following birth. Some diseases primarily affect the blood vessels; others only the heart itself.

Atherosclerosis is the major disease that affects the blood vessels. This disease may have its beginnings early in life and is first noted as a thickening of the arterial walls. This thickening is an accumulation of fat, fibrin, cellular debris and calcium. The resultant narrowing of the internal lumen of the vessel is called stenosis. Vessel stenosis impedes and reduces blood flow. Hypertension and disfunction of the organ or area of the body that suffered the impaired blood flow can result.

As the buildup on the inner wall of a vessel thickens, the vessel wall loses the ability to expand and contract. Also, the vessel loses its viability and becomes weakened and susceptible to bulging, also known as aneurysm. In the presence of hypertension, elevated blood pressure, aneurysms will frequently dissect and ultimately rupture.

Small vessels, such as the arteries that supply blood to the heart, legs, intestines and other areas of the body, are particularly susceptible to atherosclerotic narrowing. The loss of blood supply to the leg or segment of the intestine may result in gangrene. Atherosclerotic narrowing of the coronary arteries impedes, limits and in some instances prevents blood flow to regional areas of the heart. Depending upon its severity and location within the coronary circulation, pain, cardiac dysfunction or death may result.

Vascular complications produced by atherosclerosis, stenosis, aneurysm, rupture and occlusion are, in the majority of cases, managed either medically or surgically. Control and elimination of hypertension is the more effective form of medical management. In cases in which atherosclerotic disease is advanced and the attendant complications jeopardize the health of the patient, surgical intervention is usually instituted.

Aneurysms and stenosis of major arteries are best corrected by a plastic reconstruction that does not require any synthetic graft or patch materials. However, if the disease is extensive and the vessel is no longer reliable, it is usually replaced by a graft. In such cases the involved vessel section is transected and removed and a synthetic patch, conduit or graft is sewn into place.

Medium sized arteries are operated on much the same as for larger diameter vessels. But in some types of surgery where the replacement graft is of small diameter, handling and surgical placement of the graft is difficult. The internal diameter may be compromised due either to surgical technique or biological response. In some cases, the graft may become entirely occluded shortly after surgery.

Patients with coronary artery disease in which blood flow to part of the heart muscle has been compromised receive significant benefit from coronary artery bypass surgery. This type of surgery requires the use of grafts of small diameter. These grafts, the majority of which are biologic, have certain inherent problems. Synthetic grafts are only used on infrequent occasions because they are more problematical than biologic grafts. It is the purpose of this invention to obviate and eliminate certain of the more significant problems associated with the surgical procedure of coronary artery bypass and the implanted grafts following surgery.

In a patient who undergoes coronary artery bypass surgery, a non-critical artery or vein of small diameter is harvested from elsewhere in the body and sewn into place in a manner that reestablishes blood flow to the area of the heart that earlier lost its blood supply because of atherosclerotic blockage and is referred to as an autograft. When no suitable artery or vein can be harvested, an allograft or xenograft vessel may be employed. However, experience with these latter two graft types is limited because they are not readily available and the clinical results with them are not satisfactory. A synthetic graft is an alternative to an allograft or a xenograft. But, like the two biologic grafts of allograft and xenograft, the synthetic counterpart does not produce acceptable results.

Although the heart benefits immediately from the reestablished blood supply of the bypass, there is no assurance the graft will function trouble free indefinitely. The autograft, because it is harvested from the patient, who in all probability is being operated on for atherosclerotic artery disease, is high susceptible to atherosclerosis following surgery. Most harvested veins used in coronary artery bypass surgery exhibit some degree of atherosclerosis when harvested.

The long vein in the leg called the saphenous vein is the most commonly harvested vein for use as a vein bypass graft, autograft, in coronary artery surgery. Most saphenous vein bypass grafts exhibit a narrowing of the lumen unlike that of atherosclerosis. It is believed this is a pathologic response of the vein which is of different cellular construction and composition than an artery—a condition for which it is not best suited. Harvesting a saphenous vein autograft is a tedious surgical task and not always rewarded with the best quality graft. Also, removal of the saphenous vein disrupts the natural venous blood return from the leg and is not therapeutically recommended except for medical reasons such as in a patient with advanced varicose veins. Finally, harvesting an autograft in the operating room is an additional surgical time expenditure and expense.

These noted limitations of the saphenous vein autograft have generated interest in a synthetic graft for coronary artery bypass. Clinical experience with small-diameter synthetic grafts for coronary artery bypass dates back to the mid 1970's. Teflon and Dacron fibers are the most commonly employed materials for synthetic grafts. However, despite the different methods and techniques of graft construction such as woven or knit, velour, texturized or non-texturized, tight or loose, fine or course, expanded or non-expanded, variations in fiber diameter and wall thickness, etc., no graft of small lumen diameter has shown a resistance to blockage by thrombus although synthetic grafts of large diameter consistently remain patent and trouble-free for extended periods of many years. This finding is consistently repeated where a small-diameter sythetic graft is used to bypass a blocked coronary artery. Therefore, despite their inherent limitations, autografts employing the saphenous vein remain the graft of choice for coronary artery bypass surgery.

The coronary artery circulation begins with the right and left coronary artery. These two arteries in turn give rise to an extensive coronary circulation. Generally, atherosclerosis affects the larger coronary arteries. Therefore, a patient being operated upon for coronary artery disease will receive two or more vein grafts of various length and diameter depending upon the location of the blockage and the available saphenous vein.

Even though coronary artery bypass surgery is widely practiced and has become a routine procedure in hospitals throughout the world, it is not without certain operative limitations that would best be avoided. Sewing the graft to the host vessel, known as anastomosis, requires delicate surgical techniques to accomplish the best possible result. There are several complications to be avoided when anastomosing a vessel and graft together. It is important that the junction between the host tissue and graft be a uniform transition without narrowing and regional irregularities such as protuberances that bulge into the lumen or sinuses that extend outward of the lumen. A narrowing at the site of anastomosis reduces blood flow. Protuberances into the lumen obstruct blood flow and may produce turbulence. Lastly, blood that stagnates in a sinus or cavity tends to clot and obstruct the vessel lumen and subsequently the blood flow. All these characteristics diminish the effectiveness and patency of the graft.

Summarizing, the limitations associated with the autograft as applied to coronary artery bypass surgery are: tedious surgical task to harvest, physically imperfect and irregular lumen, tedious surgical task to anastomose to host vessel, physically imperfect anastomosis of irregular and unsmooth transition between graft and vessel, functional narrowing of vein graft lumen during early postoperative period, and occlusion of the autograft due to thrombosis and/or continuance of the pre-existing atherosclerotic process.

The anastomotic fitting of the present invention provides a device simplifying the surgical task of implanting coronary artery bypass grafts and of connecting two vessels to each other. The anastomotic fitting provides a connection between the ascending aorta and a graft with smooth wall contours which are not obstructive to the natural laminar flow of the blood.

SUMMARY OF THE INVENTION

The general purpose of the present invention is an anastomotic fitting for connecting a vascular graft to the ascending aorta and providing for a uniform ostium having a smooth surface throughout from the aortic wall to the graft. The anastomotic fitting includes a single flanged inflow end and at least one outflow end having at least one free end. The anastomotic fitting includes a flanged tube that inserts through a small hole in the aortic wall and engages against the inside wall, and by a fixation ring that surrounds the tube including a plurality of dual-tined anchors in rotatable position about the fixation ring that each engages into the outer aortic wall. A vascular graft engages between the external surface of the outflow end of the tube and a graft fixation collar.

According to one embodiment of the present invention, there is provided an anastomotic fitting for connection between an aortic wall and a vascular graft including a flanged tube having an aperture in the flange connecting with a longitudinal lumen extending through the tube, a plurality of aortic wall attachment ring abutments extending radially outward from the tube and adjacent to but spaced from the flange, and pluralities of graft anchor abutments spaced about a lower end of a straight portion of the tube on a plurality of circumferences; an aortic wall attachment ring having a closed ring, a plurality of spacers positioned about the ring and having an equal plurality of dual-tined anchors engaging the closed ring and separated from each other by spacers; graft fixation collar including two halves having outwardly extending projections from inner walls of the collar halves in line on a plurality of inner circumferences, proximal and distal inner rims having a plurality of peaks and valleys, and at least one recessed circumferential encircling groove about an outer periphery of the collar halves for securing the collar about the tube; and, a securing member for engagement into the recessed groove of the collar; whereby a hole is surgically positioned in the aortic wall, the flange of the flanged tube is inserted and engaged within the hole of the aortic wall, the tines of the aortic wall attachment ring are engaged into the aortic wall, the saphenous vein vascular graft is engaged over the end of the tube, and graft fixation collar halves are positioned over the vein thereby engaging the saphenous vein vascular graft between the projections on the tube and the projections and peaks and valleys on the graft fixation collar, and the other end of the saphenous graft is surgically sutured to a remote artery or connects to another anastomotic fitting of different configuration positioned in a remote artery. The anastomotic fitting can include an angular bend in the flanged tube for aligning implant.

Vascular graft is encompassing in definition including biologic grafts being either human or animal and synthetic grafts, and is not to be construed as limited to a saphenous vein graft which is discussed by way of example and for purposes of illustration only. Synthetic grafts can include woven materials of synthetic plastics, processed biologic materials, or composite metals. The vascular graft is usually of a lesser diameter than the vessel which it is being connected to, but the vessels can be of equal diameters or the vascular graft can even be of a greater diameter.

One significant aspect and feature of the present invention is a precision ostium providing for facilitated surgical implantation, and safety and efficacy in vivo. The precision nature of the flanged tube and the aortic wall attachment ring provide a high-quality and consistent ostium.

Another significant aspect and feature of the present invention is an anastomotic fitting which provides for least surgical implant time and motion, which minimizes the influences of tissue and operative variables. The steps required for surgically implanting the anastomotic fitting are simple, least time consuming, and more readily mastered than that of creating an anastomosis with a saphenous vein by the tedious hand-stitching methods.

A further significant aspect and feature of the present invention is an anastomotic fitting which can be installed in less time, with greatest efficiency, and the utilization of fewest consumable supplies, equipment and expense.

An additional significant aspect and feature of the present invention is an anastomotic fitting including several geometrical components that engage in a predetermined relationship forming an integral unit, and that are subject to no movement following surgical implant.

Having thus described the present invention, it is a principal object hereof to provide an anastomotic fitting for coronary artery grafts.

An object of the present invention is an anastomotic fitting providing an unimpeded blood flow path of smooth transitional flow contours that reduce the effects of turbulence. The flange that engages against the internal aortic wall provides minimal blood flow obstruction, turbulence and stagnation.

Another object of the present invention is an anastomotic fitting providing an external configuration that conforms with adjacent vessels and the limited space available in the chest cavity in the region of the heart.

A further object of the present invention is an anastomotic fitting including the aortic wall attachment ring that is self adjusting to local variations and thickness in the aortic wall.

An additional object of the present invention is an anastomotic fitting including a graft fixation collar that accepts saphenous vein grafts of widely varying thickness. The graft fixation collar effectively engages saphenous vein grafts of a wide range of thicknesses and retains the grafts in frictionally engaged surface contact with the outflow end of the tube providing for unrestricted natural circulation.

A still additional object of the present invention is tissue engagement of the graft by the tined anchors of the aortic wall attachment ring, the broad projections of the graft fixation collar, the lesser projections on the external surface of the free end of the tube, and the scalloped proximal and distal rims of the graft fixation collar, while the projections and rims capture or engage tissue in frictional engagement but such as not to isolate the tissue of the graft from normal circulation.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates an exploded view of an anastomotic fitting including a flanged tube, an aortic wall attachment ring, opposing collar halves of a graft fixation collar, and springs that engage the graft fixation collar;

FIG. 2 illustrates a sectional view taken along line 2—2 of FIG. 1;

FIG. 4 illustrates a sectional view of the anastomotic fitting through the aortic wall;

FIG. 5 illustrates a cutaway view of the heart and great vessels with the anastomotic fitting engaged between the wall of the ascending aorta and a saphenous vein graft;

FIG. 6 illustrates an alternative embodiment of multi-strand ligatures securing the graft fixation collar about the flanged tube;

FIG. 7 illustrates an additional embodiment of split-ring clamps engaging the graft about the flanged tube;

FIG. 8 illustrates a sectional view taken along line 8—8 of FIG. 7; and,

FIG. 9 illustrates an anostomotic fitting with a single inflow/dual outflow flanged tube.

DESCRIPTION OF PREFERRED EMBODIMENTS

Figure 3A:
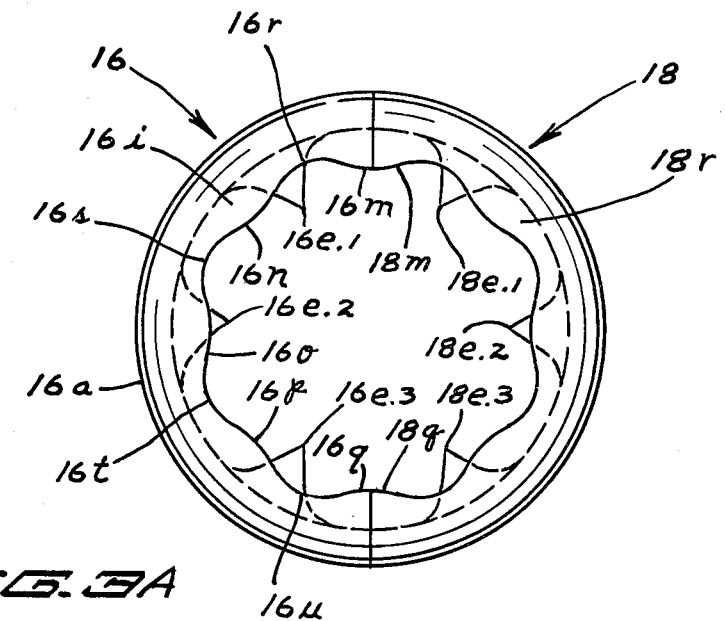
FIG. 3A illustrates a sectional view taken along line 3A—3A of FIG. 5.

FIG. 1, which illustrates an exploded view of components of an anastomotic fitting 10 of the present invention, shows a flanged tube 12 engaged in a hole 24a of an aortic wall 24, an aortic wall attachment ring 14, graft fixation collar including halves 16 and 18 which are mirror images of each other, and springs 20 and 22 for securing and engaging the graft fixation collar halves 16 and 18 about a saphenous vein 26 engaged over the flanged tube 12 as illustrated in FIG. 4 and as later described in detail. Flanged tube 12 includes a flange member 12a including an aperture 12b having a rounded interior edge 12c and rounded outer edge 12d, and a longitudinal tube 12e including an angular bend 12f, a rounded outer edge 12g, a plurality of outwardly extending aortic wall attachment ring (AWAR) abutments 12h–12m positioned adjacent to but spaced from the flange 12a and as also illustrated in FIG. 2, graft anchor projections 12n and 12p spaced about a lower end of the tube 12e in circumferential rows 12o and 12q where each row includes six projections, and a longitudinal lumen 12r running through the tube 12e. The number of AWAR abutments and graft anghor projections is by way of example and for purposes of illustration only, and is not to be construed as limiting of the present invention. The flange 12a and wall of the tube 12e are constructed as an inseparable, integral unit and are made as thin as possible but yet maintaining dimensional stability, thereby minimizing structural weight for least space. Suitable materials by way of example are titanium, tantalum, stainless steel, Pyrolite, ceramic, sapphire. Thickness can range from 0.003 inch to 0.03 inch. The angular relationship between the plane of the flange 12a and the tube 12e can be in the range of 20°–90°, and preferably 30°. The flange 12a can vary in geometrical configuration from a flat planar member to a member having curvature corresponding to the internal aortic wall. The AWAR abutments 12h–12m extend in the range of 1.50 millimeters (mm) from the exterior surface of the tube 12e outward in a plane parallel to the flange 12a and spaced from the flange in the range of 3.0 mm. The graft anchor projections 12n and 12p are asymmetrically spaced and can number from four to sixteen. The projections 12n and 12p extend in the range of 0.5 mm above the surface of the tube, and have a width and length of 0.5 mm and 1.5 mm respectively.

Aortic wall attachment ring (AWAR) 14 includes a closed ring 14a, a plurality of circular spacers 14b–14n having a finite width, as illustrated in FIG. 2, and an equal plurality of dual-tine anchors 14n–14y, as illustrated in FIG. 2. The number of spacers and number of dual-tine anchors is by way of example and for purposes of illustration only. The closed ring 14a is circular having a diameter slightly larger than the external outer diameter of the tube 12e positioned between the flange 12a and abutments 12h–12m, and having a square cross-section with rounded corners. The internal diameter of each spacer is slightly larger than the cross-sectional dimension of the closed ring with a wall of the spacer being 0.25 mm or less. The dual-tine anchors 14n–14y are substantialy U-shaped with the outer leg 14n.1 being longer than the inner leg 14n.2; each of the legs includes a substantially 90° bend with both bends being in the same plane, and the ends of the anchors being substantially pointed. The points can be spaced up to the range of 2-3 mm.

The AWAR 14 can be assembled by stringing a predetermined number of spacers of a predetermined length onto the preformed open ring having a square cross-section. The two ends of the open ring are then joined together and welded thereby forming a closed ring and capturing the spacers. One open dual-tined anchor is looped around the closed ring between each spacer where the long tine of the anchor is permanently bent into position over the short tine resulting in loose capture about the closed ring. The process is repeated for each dual-tined anchor.

The AWAR 14 can be assembled on the flanged tube 12 by initially encircling the tube 12e between the flange and the abutments with the preformed open ring, and then proceeding as described in the preceding paragraph. In the alternative, the AWAR 14 is assembled independently as described in the preceding paragraph, and then the AWAR 14 is positioned over the inflow end of the tube 12e, and the flange 12a is subsequently formed by impact or spinning techniques. The AWAR 14 should have a slight clearance about the tube 12e in the range of 0.3-0.4 mm. The components of the AWAR 14 must be composed of a rigid material including metals or plastics.

Graft fixation collar (GFC) including halves 16 and 18 are mirror images of each other and hence only one is described. The graft fixation collar 16 includes a right cylinder member 16a, having an internal bore 16b and a length approximated to the straight line section of tube 12e, pluralities of sharp projections 16c, 16d and 16e from the internal surface arranged about three internal projection circumferences 16f, 16g and 16h, a proximal rim 16i having a scalloped circumference including peaks and valleys, and a distal rim 16j having a scalloped circumference including peaks and valleys. The internal bore 16b includes the pluralities 16c, 16d, 16e of projections in the range of six to eight about each internal projection circumference 16f, 16g, 16h, which penetrate and engage the graft, and also serve to frictionally engage against the surface of the tube 12e. The peaks of the rims 16i and 16j engage the graft. The external surface of the graft fixation collar 16 includes two encircling circumferential, recessed engagement grooves 16k and 16l for accepting structure for securing the two collar havles 16 and 18 either by the springs 20 and 22 of FIG. 1, ligatures of FIG. 6, or by the split ring of FIGS. 7 and 8. The recessed grooves have dimensions in the range of 1.5 mm wide by 0.8 mm deep. The graft fixation collar can be constructed from the same material as the flanged tube including metals. Pyrolite, sapphire or ceramic, and plastics such as polycarbonate, polysulfane, Teflon and others. All numbers corresponding to GFC 18 are identical to the elements and numerals previously described for GFC 16.

Springs 20 and 22 can be either an endless coil spring in the form of a toroid or a double-ended coil. Each end of a double-ended spring is terminated in the form of a loop or hook. The spring can be either a coil of closed or open turns having a diameter slightly smaller than the width of the engagement grooves. The scalloped rims 16h and 16i are intended to exert intermittent but gentle pressure on the graft as it lies between the scalloped rims and the surface of tube 12e. The springs are of a suitable metal having a predetermined spring constant and, likewise, the GFC is constructed of like material for eliminating electrochemical interaction with the blood and other component parts.

FIG. 2, which illustrates a sectional view taken along line 2—2 of FIG. 1, shows the aortic wall 24, the AWAR abutments 12h–12m about the tube 12e, the AWAR ring 14a, spacers 14b–14m, and dual-tined anchors 14n–14y.

FIG. 3A, which illustrates a sectional view of the GFC halves 16 and 18 taken along line 3A—3A of FIG. 5, shows the proximal rim 16i and 18i including respective peaks 16m–16q and valleys 16r–16u and the top projections 16e.1–16e.3 from the internal surface of the halves of the graft fixation collar 16. Numerals corresponding to GFC 18 are applicable to the elements and numerals previously described for GFC 16.

Figure 3B:
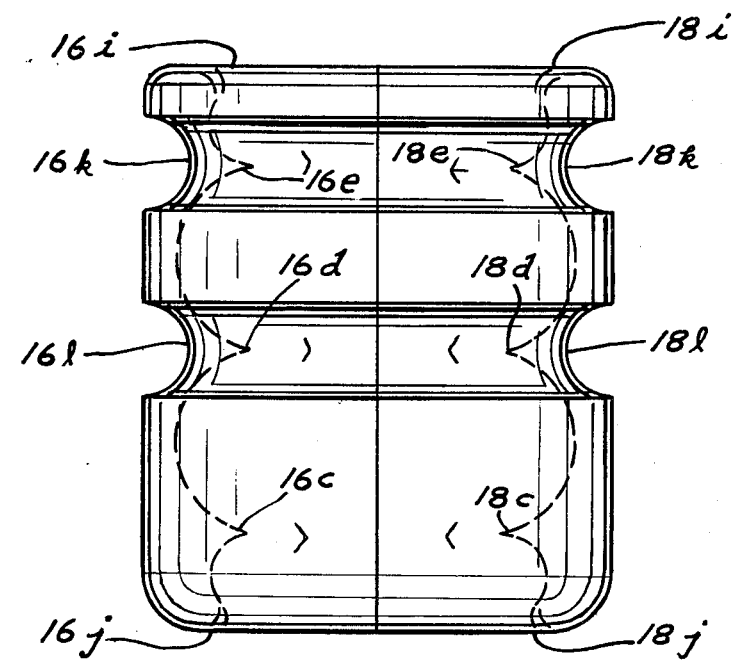
FIG. 3B illustrates a side view of the graft fixation collar.

FIG. 3B, which illustrates a side view of the graft fixation collar halves 16 and 18, shows the proximal rim 16i and 18i including a scalloped interior circumference, a distal rim 16j and 18j including a scalloped interior circumference, recessed encircling circumferential grooves 16k, 18k, 16l, 18l, and the pluralities of outward extending projections 16c, 16d, 16e from the interior surface of the graft fixation collar along three interior circumferences 16f, 16g, and 16h as illustrated in FIG. 1.

MODE OF OPERATION

Anastomotic fitting or fittings which are to be implanted are predetermined by the location of the coronary artery blockage, surgical accessibility of the downstream coronary arteries, and size of the downstream coronary arteries where a graft or grafts are implanted for best surgical result. While in most cases a surgon will implant three or more bypass grafts in each patient who undergoes coronary artery bypass surgery, for purposes of illustration and for example only the description of the mode of operation is limited and directed to an implant of one bypass graft, and is not to be construed as limiting of the present invention as the description can be extended to more than one bypass graft implant as required.

FIGS. 5 and 4 illustrate a plan view of the anastomotic fitting through the aortic wall and a sectional view respectively of the anastomotic fitting 10 engaged on the aortic wall of a human respectively.

Anastomotic fittings can be sized according to the internal diameter of the tube 12e. For purposes of example and illustration, a size 3 model has a tube 12e having a 3 mm internal diameter. Models of size 3, 4, 5 and 6 are required for present coronary bypass. A size 3 model has a 3 mm internal diameter and a 4.5 mm external diameter. A size 3 model includes an AWAR 14 with 8-12 tined anchors. For purposes of example and illustration, a size 3 model has an AWAR 14 with ten anchors having a closed ring with a diameter of 5.9 mm where each of the ten spacers has a width of 1.26 mm and where each of the ten tined anchors has a width of 0.3 mm. The GFC minimum internal diameter is substantially equal to the external diameter of the tube 12e and the external diameter is slightly less than twice the minimum internal diameter. The length of the GFC approximates the length of a straight section of the tube 12e. For a size 3 model, the GFC includes a 4.5 mm minimum internal diameter, substantially 8 mm external diameter, and approximately 9-10 mm long.

A saphenous vein graft having a lumen diameter of approximately 4 mm is to be implanted for coronary bypass surgery. A size 3 anastomotic fitting has a 4.5 mm external diameter as previously described and is best suited for this particular graft. It is noted that available graft size is not the only determining factor in coronary bypass surgery as there are other biologic considerations that are medical and/or surgical in nature which must be taken into account.

Referring to FIG. 5, with the patient on cardiopulmonary bypass, a 4.0-4.5 mm round hole 24a is made at a predetermined site in the wall of the ascending aorta using an instrument designated for this procedure. Next, the outflow end of the size 3 flanged tube 12 is grasped between the thumb and forefinger, and wetted with blood. Holding the flange 12a at an acute angle of about 45° to the aortic wall, the leading edge of the flange 12a is carefully inserted into the hole 24a. In a continual arcuate or turning motion, the trailing edge of the flange 12a is eased through the hole. Two factors facilitate insertion of the large diameter flange through the small diameter hole in the aortic wall. First, the blood acts as a lubricant for easing the motion required for inserting the flange through the hole. Second, the elasticity of the aortic wall causes the hole to relax and admit the passage of the large diameter flange. Continuing to grasp the free end of the tube 12e between the thumb and forefinger, the flanged tube 10 is retracted gently causing the flange to engage against the aortic wall. Individually, the long tines of each of the anchors 14n-14y are grasped between the jaws of a curved surgical instrument such as a hemostat or forceps and firmly advanced into the thickness of the aortic wall, as illustrated in FIG. 4. This is done by rotating each of the anchors 90° on the closed ring. This 90° rotation of the anchor from the disengaged position into the engaged position provides for engagement of each anchor regardless of the natural variations in the aortic wall. Rotation is achieved in that the width of the U segment of the anchor is slightly larger than the cross-section of the closed ring which the segment encircles providing for rotation in a disengaged position and for locking frictional engagement in a loaded state when engaged into the aortic wall. The anchor inherently functions as a spring based on the free-ended tine structure and the curvature at the bottom of the U segment. The flanged tube 12 is secured to the aortic wall after all the anchors have been rotated and engaged into the outer aortic wall. If the placement of an anchor is unsuitable, the anchor is easily withdrawn by reversing it 90° and rerotating the anchor into the desired position.

Connection of the saphenous vein graft 26 to the flanged tube 12 and placement of the graft fixation collar halves 16 and 18 over the straight end of the flanged tube 12 is the remaining step. The distal anastomosis is not an integral step in the use of the anastomotic fitting and, therefore, it is not considered in depth in this example. The saphenous vein or vascular graft 26 is tailored to a predetermined proper length, and positioned between the distal and proximal anastomotic sites in a relaxed state free of twists or kinks. The outflow end of the flanged tube is wetted with blood or other medical lubricant to ease passage of the saphenous vein graft 26 over the flanged tube to a length of 9-10 mm. Care is taken to ensure that the portion of the saphenous vein graft over the straight segment of the flanged tube is not under compression, bunched, or unduly elongated. This provides proper placement and fit of the graft fixation collar, and that the saphenous vein graft is of correct length between the end of the flanged tube and the distal anastomosis, a most important factor.

The halves 16 and 18 of the graft fixation collar are positioned over the saphenous vein graft 26 from opposite directions. Care is taken to avoid any gaps between opposing surfaces of the GFC halves of pinching of the saphenous vein graft. Proper positioning is obtained by grasping the GFC between the thumb and forefinger, and exerting gentle pressure for setting the graft penetrating projections. Finally, the chosen retainer of coil springs 20 and 22 are positioned, one in each groove of the graft fixation collar. If a continuous coil spring is selected, the coil is expanded between two surgical instruments such as forceps and advanced over the GFC, positioned in the appropriate groove, and released. If instead a double-ended coil spring is chosen, the coil is applied by looping the coil around the GFC, positioning the coil in the groove, extending it under slight tension, and hooking the ends of the coil together.

The coil spring either of a continuous coil or a double-ended coil is the preferred retainer because the coils provide constant tension to the GFC and the underlying saphenous vein graft. Also, a spring is easily and more quickly installed than other types of retainers.

The graft fixation collar is held in position on the flanged tube by frictional engagement between the ends of the numerous sharp projections 16c, 16d and 16e in the range of 18 to 24 and the exterior surface of the tube. The smaller projections 12n and 12p asymmetrically located on the exterior surface of the flanged tube physically engage the sharp projections of the GFC, arresting any dislodgement movement of the GFC.

The scalloped rim 16j at the distal end of the GFC provides for gentle holding of the vein graft 26 in close approximation with the outflow end or rim of the flanged tube. This ensures minimal transition between the internal wall of the flanged tube and that of the graft. A minimal surface transition at the interface between the tube and graft is desirable because it will promote laminar flow and reduce stagnation.

ALTERNATIVE EMBODIMENT—LIGATURES SECURING OF GRAFT FIXATION COLLAR

FIG. 6 illustrates an alternative embodiment of a graft fixation collar, partially cutaway, with two multi-strand ligatures 30 and 32 securing the collar halves 16 and 18 about the saphenous vein graft 26 to the outflow end of the anastomotic fitting. Multi-strand ligatures 30 and 32 are positioned in the engagement grooves 16k, 16L, 18k and 18L and are secured about the collar with surgical knots. The function of the multi-strand ligatures is equivalent to that of the springs.

The operation and implantation of the anastomotic fitting is identical to that as previously described for FIGS. 1-5, and the only operating procedure is the surgical tying of the ligatures about the graft fixation collars in lieu of the coil springs.

ALTERNATIVE EMBODIMENT—SPLIT-RING CLAMP SECURING OF GRAFT FIXATION COLLAR

FIG. 7, which illustrates an alternative of embodiment of split-ring clamps 34 and 36 engaging the graft directly about the flanged tube, shows two opposing offset split-ring collars which engage over the graft in opposing relationship with respect to each of the split-ring collars so that the clamps overlap assuring 360° clamping of the saphenous vein graft 26.

FIG. 8, which illustrates a sectional view taken along line 8—8 of FIG. 7, shows a top view of a split ring having a partial 210° circular ring 36a and a plurality of centrally extending inward projections in the range of 3 mm. In this example, the split ring includes nine inwardly extending projections 36b–36j where each projection includes a sharp point.

The operation and implantation of the anastomotic fitting is identical to that as previously described for FIGS. 1–5, and the only operative procedure is surgical clamping of the clamps directly securing the graft to the flanged tube absent the graft fixation collar halves.

ALTERNATIVE EMBODIMENT—ANASTOMOTIC FITTING WITH SINGLE INFLOW/DUAL OUTFLOW ENDS

FIG. 9, which illustrates an anastomotic fitting 40 with a single inflow orifice 40a and dual outflow orifices 40b and 40c, is useful in cases where two saphenous vein grafts are implanted. The two free-ended outflow orifice tubes 40b and 40c are in a plane which forms an acute angle in the range of 15°–90° with the plane of the flange, or more preferably, an angle in the range of 20°–40°. In this example and for purposes of illustration only, the outflow tubes diverge at an angle of 30°. The additive cross-sectional area of both tubes approximates the cross-sectional area of the inflow tube. The thickness of the flange and thickness of the walls of the tubes of the dual-orifice device is substantially the same as the single-orifice device and is constructed of the same materials. The dual-orifice fitting utilizes the same aortic wall attachment ring and graft fixation collar as the single-orifice device. Surgical implant technique for the dual-orifice device is identical to that of the single-orifice device. All other numerals correspond to the elements previously described.

The operation and implantation of the dual-outflow orifice anastomotic fitting is identical to that as previously described for FIGS. 1–5 with the inclusion that two vascular grafts are connected to the dual-outflow orifice and that the coil springs, ligatures, or clamps can be utilized to secure the graft fixation collar about each outflow orifice.

Various modifications can be made to the anastomotic fitting of the present invention without departing from the apparent scope thereof. The graft can be either biologic or synthetic. The retainers about the graft fixation collar halves can take any of the previous disclosed forms having a predetermined spring constant. The dual-tine anchors can be a single-tine anchor. Other suitable aortic wall attachment ring structure can be substituted for the disclosed AWAR 14. The graft fixation collar can be omitted as illustrated in FIG. 7, and coil springs or ligatures utilized in lieu of the spring clamps. In the alternative, spring clamps can be utilized with graft fixation collar halves with dimensions being determined accordingly.

Having thus described the invention, what is claimed is:

1. Anastomotic fitting for reconnecting a vessel or connecting a vessel of a first diameter to a vessel of a second diameter comprising:
   a. means for engaging in a hole between an inner and outer wall of a first diameter vessel including an inflow orifice and at least one outflow orifice, and means for holding a second diameter vessel at said outflow orifice, said engaging means including a flanged tube, an aperture in a flange at said inflow orifice, plurality of radial wall attachment ring abutments extending outwardly from said tube and adjacent but spaced from said flange, and a plurality of circumferential rows of alternating geometrically configured outward extending projections about a distal portion of said outflow orifice end of said tube;
   b. means for securing said engagement means to said wall of said vessel of said first diameter including a plurality of independently rotatable dual tined anchor attachment means supported on a ring of predetermined geometrical cross section adjacent said flange and spaced by spacers alternating with each of said tined means and adjacent to said engaging means, said securing means being positionable from an unengaged position to an engaged position into the wall of said vessel of said first diameter by rotating each of said dual tined anchor attachment means about said ring;
   c. means for collaring said vessel of said second diameter to said outflow orifice of said engagement means, said collaring means including two cylindrical mirror-image halves, at least two circumferential rim projections extending inwardly from interior surfaces of said halves, and at least two recessed grooves about outer circumferences of said halves; and,
   d. means for securing said collar means adjacent said outflow orifice with said vessel of said second diameter about said recessed grooves of said collar means therebetween whereby said anastomotic fitting provides a surgical connection between said vessel of said first diameter and said vessel of said second diameter.

2. Anastomotic fitting of claim 1 wherein said longitudinal tube comprises two longitudinal outflow orifice tubes connecting to said aperture.

3. Anastomotic fitting of claim 1 wherein said securing means comprises an endless closed-end spring engaged in said grooves.

4. Anastomotic fitting of claim 1 wherein said securing means comprises a double-ended spring engaged in said grooves.

5. Anastomotic fitting of claim 1 wherein said securing means comprises multi-strand ligatures engaged in said grooves.

6. Anastomotic fitting of claim 1 wherein said securing means comprises split-ring clamps engaged in said grooves.

7. Anastomotic fitting of claim 1 wherein said vessel of said first diameter is of a larger diameter than said vessel of said second diameter.

8. Anastomotic fitting of claim 1 wherein said vessel of said second diameter is a vascular graft.

9. Anastomotic fitting for coronary bypass surgery and for connecting a graft to an aorta, said anastomotic fitting comprising:
   a. flanged tube including an aperture in said flange connecting with a hole through said tube, a plurality outwardly extending aortic wall attachment ring abutments on said tube and adjacent to but spaced from said flange and positioned adjacent said flange, and pluralities of circumferential rows of graft anchor geometrically configured projections pointed toward and spaced about a lower outflow distal end of said tube;
   b. aortic wall attachment ring including a closed ring having a substantially rectangular cross-section, and a plurality of alternating spacers and anchors positioned about said closed ring, said closed ring positioned between said flange and said abutments, said anchors being dual tined and independently rotatable on said ring from an unengaged position to an engaged position into the wall of the aorta;

c. graft fixation collar including two cylindrical mirror-image halves, each of said two halves includes pluralities of inwardly extending rim projections providing escalloped circumferences of peaks and valleys from said inner walls and at least two recessed grooves in an outer circumference; and, d. retaining means having a predetermined spring constant for securing about said collar halves on said groove whereby said flanged tube is engaged in a hole in said aorta and said flange engages against an inner aortic wall, said aortic wall attachment ring anchors against an outer aortic wall, said graft engages over said tube of said flanged tube, said graft fixation collar halves engage over said graft and said retaining means secures said graft between said collar halves and said tube thereby providing a surgical implant and connection of said anastomotic fitting between said aortic wall and said graft.

10. Anastomotic fitting of claim 9 wherein said pluralities of graft anchor projections comprise two rows.

11. Anastomotic fitting of claim 9 wherein each of said dual-tined anchors include pointed ends and include an outer tine longer than the inner tine.

12. Anastomotic fitting of claim 9 wherein said plurality of inward projections of said graft fixation collar comprises three circumferences of pluralities of projections.

13. Anastomotic fitting of claim 9 wherein said grooves are positioned on an upper mid portion of said collar.

14. Anastomotic fitting of claim 9 wherein retaining means comprises spring.

15. Anastomotic fitting of claim 9 wherein said retaining means comprises multi-strand ligature.

16. Anastomotic fitting of claim 9 wherein said retaining means comprises split-ring clamp.

* * * * *